(12) United States Patent
Carbone et al.

(10) Patent No.: US 8,981,165 B2
(45) Date of Patent: Mar. 17, 2015

(54) PRODUCTION OF ALCOHOLS HAVING THREE CARBON ATOMS FROM CARBONACEOUS MATERIALS

(75) Inventors: Anthony S. Carbone, Montreal (CA); Stephane Marie-Rose, Sherbrooke (CA); Esteban Chornet, Sherbrooke (CA)

(73) Assignee: Enerkem, Inc., Montreal, Quebec (CA)

( * ) Notice: Subject to any disclaimer, the term of this patent is extended or adjusted under 35 U.S.C. 154(b) by 0 days.

(21) Appl. No.: 13/568,582

(22) Filed: Aug. 7, 2012

(65) Prior Publication Data

US 2013/0158299 A1 Jun. 20, 2013

Related U.S. Application Data

(60) Provisional application No. 61/573,906, filed on Sep. 14, 2011.

(51) Int. Cl.

| | | |
|---|---|---|
| *C07C 29/04* | (2006.01) | |
| *C07C 29/16* | (2006.01) | |
| *C01B 3/32* | (2006.01) | |
| *C07C 29/141* | (2006.01) | |
| *C07C 29/151* | (2006.01) | |
| *C07C 41/09* | (2006.01) | |
| *C10J 3/46* | (2006.01) | |
| *C10K 1/00* | (2006.01) | |
| *C10K 3/04* | (2006.01) | |

(52) U.S. Cl.
CPC ............ *C07C 29/16* (2013.01); *C07C 29/04* (2013.01); *C01B 3/32* (2013.01); *C07C 29/141* (2013.01); *C07C 29/1518* (2013.01); *C07C 41/09* (2013.01); *Y02E 50/18* (2013.01); *Y02E 50/32* (2013.01); *C01B 2203/0415* (2013.01); *C01B 2203/0465* (2013.01); *C01B 2203/0485* (2013.01); *C01B 2203/061* (2013.01); *C10J 3/463* (2013.01); *C10K 1/003* (2013.01); *C10K 3/04* (2013.01); *C10J 2300/0916* (2013.01); *C10J 2300/0956* (2013.01); *C10J 2300/0976* (2013.01); *C10J 2300/0993* (2013.01); *C10J 2300/1665* (2013.01); *C01B 2203/02* (2013.01)
USPC ........... 568/896; 568/897; 568/898; 568/899; 568/900; 568/901; 568/909

(58) Field of Classification Search
CPC ...................................................... C07C 29/04
USPC .......... 568/896, 897, 898, 899, 900, 901, 909
See application file for complete search history.

(56) References Cited

U.S. PATENT DOCUMENTS

2009/0326080 A1   12/2009   Chornet et al.

FOREIGN PATENT DOCUMENTS

| BR | 20007000631 A | * 10/2008 |
|---|---|---|
| WO | 2009132449 A1 | 11/2009 |
| WO | 2010069068 A1 | 6/2010 |

* cited by examiner

*Primary Examiner* — Elvis O Price
(74) *Attorney, Agent, or Firm* — Raymond J. Lillie

(57) ABSTRACT

A process for producing alcohols having three carbon atoms from carbonaceous materials such as biomass. The carbonaceous material, such as biomass, is gasified to produce synthesis gas. The synthesis gas then is subjected to a plurality of reactions to produce alcohols such as n-propanol and isopropanol.

36 Claims, 1 Drawing Sheet

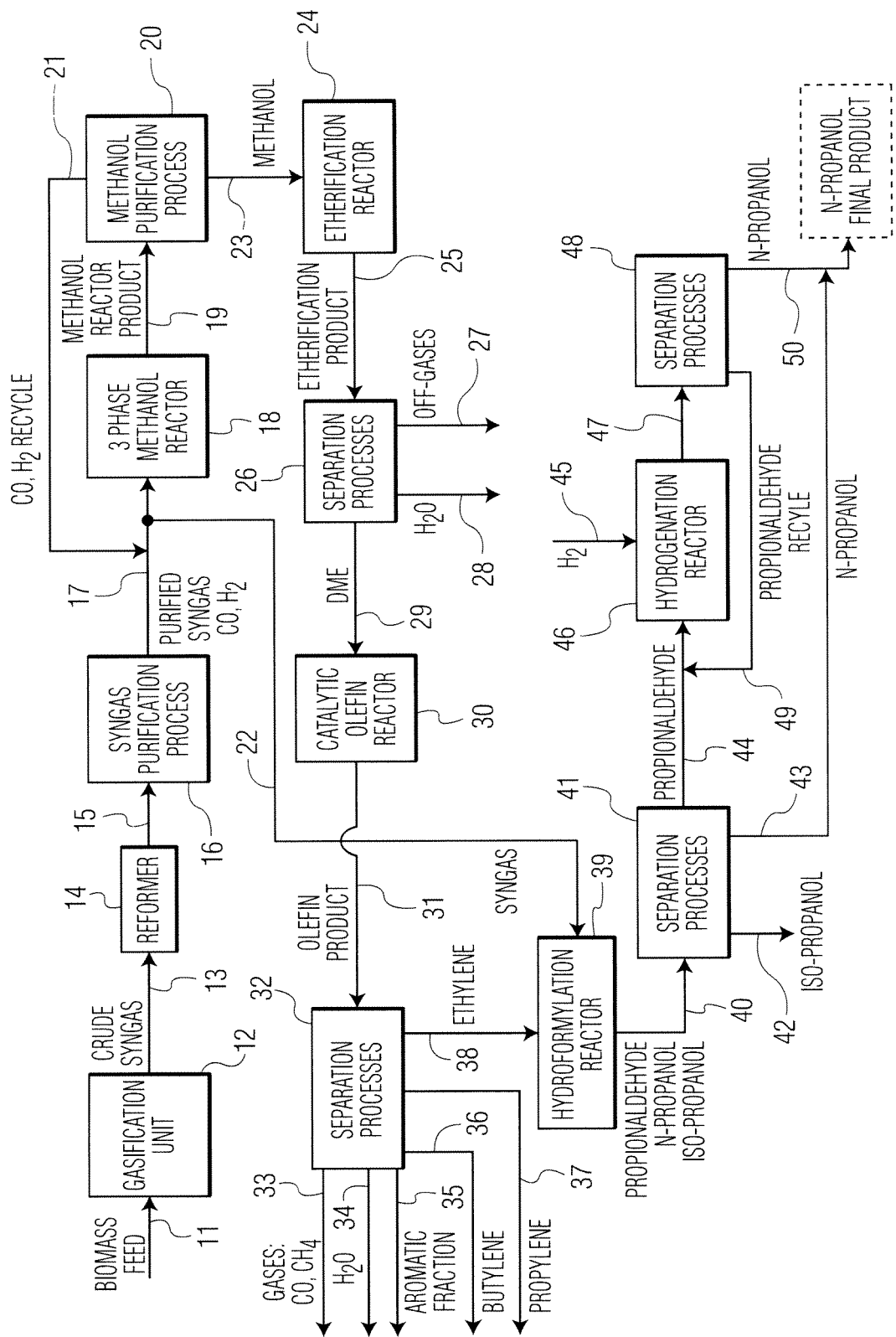

PRODUCTION OF ALCOHOLS HAVING THREE CARBON ATOMS FROM CARBONACEOUS MATERIALS

This application claims priority based on provisional Application Ser. No. 61/573,906, filed Sep. 14, 2011, the contents of which are incorporated by reference in their entirety.

This invention relates to the production of alcohols from carbonaceous materials, such as biomass, municipal solid wastes, and industrial waste materials. More particularly, this invention relates to gasifying carbonaceous materials to produce synthesis gas, and to producing alcohols having three carbon atoms from such synthesis gas.

Synthesis gas, or syngas, includes carbon monoxide (CO) and hydrogen ($H_2$), with small amounts of carbon dioxide and residual hydrocarbons, and has a variety of uses. Synthesis gas may be used as a fuel gas in internal combustion engines, in gas turbines, as well as in gas fired steam boiler plants, or may be used to produce other desired materials, such as methanol and ethanol.

Synthesis gas may be produced by gasifying carbonaceous materials, such as residual biomass materials, such as forest residues agricultural residues, spent structural wood materials, and urban biomass, such as municipal solid waste, and industrial solid waste. The gasification of such materials provides a crude synthesis gas. The crude synthesis gas may be purified to remove impurities such as ammonia ($NH_3$), sulfur compounds (such as hydrogen sulfide ($H_2S$) and carbonyl sulfide (COS), chlorine compounds (such as HCl), volatile metals, tars, fines (in the form of sub-micron particles containing metals and metal salts), and char (solid particulates typically above 0.001 mm and containing carbon, metals, and metal salts). The purified syngas then may be used as a fuel or be used to produce other materials.

In accordance with an aspect of the present invention, there is provided a process for producing at least one alcohol having three carbon atoms from a carbonaceous material. The process comprises gasifying the carbonaceous material to provide a crude synthesis gas. The crude synthesis gas then is purified to provide a purified synthesis gas. At least a portion of the carbon monoxide and at least a portion of the hydrogen from the purified synthesis gas then are reacted to produce methanol. The methanol then is reacted under conditions to provide a product comprising dimethyl ether. The dimethyl ether then is reacted under conditions to provide ethylene. The ethylene is reacted with synthesis gas in a hydroformylation reactor to provide a product comprising at least one alcohol having three carbon atoms. The at least one alcohol having three carbon atoms then is recovered from such product.

In a non-limiting embodiment, the carbon monoxide and hydrogen from a first portion of the purified synthesis gas are reacted to produce methanol, and then the methanol is reacted under conditions to provide a product comprising dimethyl ether, which then is reacted under conditions to provide ethylene as hereinabove described. The ethylene then is reacted with a second portion of the purified synthesis gas in a hydroformylation reactor to provide a product comprising the at least one alcohol having three carbon atoms.

In another non-limiting embodiment, essentially all of the carbon monoxide and essentially all of the hydrogen of the purified synthesis gas are reacted to produce methanol. The methanol then is reacted under conditions to provide a product comprising dimethyl ether, which then is reacted under conditions to provide ethylene. The ethylene then is reacted with a synthesis gas, other than the purified synthesis gas obtained by gasifying the carbonaceous material hereinabove described, in a hydroformylation reactor to provide a product comprising at least one alcohol having three carbon atoms. In a non-limiting embodiment, the synthesis gas which is reacted with the ethylene is obtained by subjecting natural gas to steam reforming to provide a crude synthesis gas, which then is purified.

In a non-limiting embodiment, the ethylene is reacted in a hydroformylation reactor to produce a product which comprises, in addition to the at least one alcohol having three carbon atoms, propionaldehyde. The propionaldehyde is hydrogenated to provide additional at least one alcohol having three carbon atoms. Alcohols having three carbon atoms which may be produced in accordance with the present invention include, but are not limited to, n-propanol and isopropanol.

In a non-limiting embodiment, the at least one alcohol is n-propanol. In another non-limiting embodiment, the at least one alcohol further comprises isopropanol.

Carbonaceous materials which may be gasified in accordance with the present invention include, but are not limited to, biomass-rich materials.

Biomass-rich materials which may be gasified in accordance with the present invention include, but are not limited to, homogenous biomass-rich materials, non-homogeneous biomass-rich materials, heterogeneous biomass-rich materials, and urban biomass.

In general, homogeneous biomass-rich materials are biomass-rich materials which come from a single source. Such materials include, but are not limited to, materials from coniferous trees or deciduous trees of a single species, agricultural materials from a plant of a single species, such as hay, corn, or wheat, for example, primary sludge from wood pulp, and wood chips.

Non-homogeneous biomass-rich materials in general are materials which are obtained from plants of more than one species. Such materials include, but are not limited to, forest residues from mixed species, and tree residues from mixed species obtained from debarking operations or sawmill operations.

Heterogeneous biomass-rich materials in general are materials that include biomass and non-biomass materials such as plastics, metals, and/or contaminants such as sulfur, halogens, or non-biomass nitrogen contained in compounds such as inorganic salts or organic compounds. Examples of such heterogeneous biomass-rich materials include, but are not limited to, urban biomass such as municipal solid waste, such as refuse derived fuel, solid recovered fuel, sewage sludge, used electrical transmission poles and railroad ties, which may be treated with creosote, pentachlorophenol, or copper chromium arsenate, and wood from construction and demolition operations which may contain one of the above chemicals as well as paints and resins.

In a non-limiting embodiment, prior to the gasification of the biomass, the biomass is admixed with at least one additive material, which neutralizes impurities such as chlorine, fluorine, and sulfur, which may be present in the biomass. In a non-limiting embodiment, the at least one additive is at least one adsorbent material. Such adsorbent materials include, but are not limited to, calcium oxide, or mixtures of calcium oxide, calcined limestone, ash materials, olivine (a silicate of iron and magnesium), and mixtures of calcium and magnesium oxides.

In another non-limiting embodiment, the at least one additive material is added to the biomass in an amount of from about 1.25 to about 3.0 times the stoichiometric quantity required for full neutralization of chlorine and other halogens, as well as sulfur present in the biomass. The term "neutralization," as used herein, includes the formation of stable salts such as $CaCl_2$, $CaF_2$, $CaS$, and the corresponding salts of magnesium and iron.

Gasification of the carbonaceous material, such as biomass, may be effected by means known to those skilled in the art. For example, in a non-limiting embodiment, the biomass may be gasified in a gasifier which includes a fluidized bed section and a reforming, or freeboard, section. Examples of such gasifiers are disclosed in published PCT Application Nos. WO2009/132449 and WO2010/069068.

In a non-limiting embodiment, the carbonaceous material, such as biomass, in a first step, is contacted in the fluidized bed section of the gasifier under conditions which effect a partial oxidation of the biomass. As a result of the partial oxidation, the biomass decomaposes thermally, and there are produced a solid carbonaceous residue, gases, such as $CO_2$, steam, and some carbon monoxide and hydrogen, and vapors of intermediate species such as low molecular weight alkyl and aromatic hydrocarbons, and phenolics such as phenol, catechols, and methoxylated, alkylated, and alkoxylated phenols.

In a non-limiting embodiment, the biomass, in a first step, is heated in the fluidized bed section of a gasifier to a temperature of at least 500° C. and no greater than 1,000° C. In another non-limiting embodiment, the biomass, in the first step, is heated to a temperature of at least 550° C. and no greater than 900° C. In another non-limiting embodiment, the biomass, in the first step, is heated to a temperature of at least 600° C. and no greater than 800° C. In a further non-limiting embodiment, the biomass, in the first step, is heated to a temperature of at least 600° C. and no greater than 700° C. In yet another non-limiting embodiment, the biomass, in the first step, is heated to a temperature of about 690° C.

In a non-limiting embodiment, the oxidizing gas, in the first step, further comprises nitrogen in an amount which does not exceed 80 vol. % of the oxidizing gas. In one non-limiting embodiment, the oxidizing gas includes oxygen. In a non-limiting embodiment, oxygen is present in an amount of from about 5 vol. % to about 100 vol. % of the oxidizing gas, and nitrogen is present in an amount that does not exceed 80 vol. % of the oxidizing gas. In another non-limiting embodiment, the oxidizing gas includes oxygen-enriched air and steam.

In another non-limiting embodiment, the biomass, in the first step, is contacted with an oxidizing gas that includes oxygen in the absence of nitrogen. In a non-limiting embodiment, oxygen is present in such nitrogen-free gas in an amount of from about 5 vol. % to about 100 vol. %. In another non-limiting embodiment, the oxidizing gas further includes steam. In another non-limiting embodiment, oxygen is present in an amount of from about 5 vol. % to about 40 vol. %. In yet another non-limiting embodiment, oxygen is present in such nitrogen-free gas in an amount of from about 30 vol. % to about 40 vol. %.

In another non-limiting embodiment, the oxidizing gas, in the first step, includes carbon dioxide. Carbon dioxide may be present in a non-limiting embodiment, in an amount of from about 5 vol. % to about 100 vol. %. In a further non-limiting embodiment, carbon dioxide is present in the oxidizing gas in an amount of from about 5 vol. % to about 40 vol. %. In yet another non-limiting embodiment, carbon dioxide is present in the oxidizing gas in an amount of from about 10 vol. % to about 20 vol. %.

In a further non-limiting embodiment, oxygen is present in the oxidizing gas, in an amount of from about 30 vol. % to about 40 vol. %, carbon dioxide is present in the oxidizing gas in an amount of from about 10 vol. % to about 20 vol. %, and the remainder of the oxidizing gas essentially is steam. Trace amounts of argon may be present.

In another non-limiting embodiment, the biomass, in the first step, is contacted with oxygen at a weight ratio of oxygen to biomass is from about 0.1 to about 0.5 times the stoichiometric weight ratio needed for complete combustion, i.e., total oxidation of the biomass.

In a further non-limiting embodiment, the biomass, in the first step, is contacted with oxygen at a weight ratio of oxygen to biomass of from about 0.2 to about 0.35 weight of the stoichiometric weight ratio needed for complete combustion of the biomass. In yet another non-limiting embodiment, the biomass is contacted with oxygen at a weight ratio of oxygen to biomass of from about 0.25 to about 0.30 of the stoichiometric weight ratio needed for complete combustion of the biomass.

In another non-limiting embodiment, in the first step, the biomass is contacted with oxygen and steam in a bed of particulate material, whereby the passage of oxygen and steam through such bed provides a fluidized bed of the particulate material. Such particulate materials include, but are not limited to, alumina, olivine, silica, anthracite, desulfurized petroleum coke, and in general, any stable refractory material. In a non-limiting embodiment, the particulate material is selected from the group consisting alumina, olivine and silica. In another non-limiting embodiment, the particles have a diameter of from about 50 microns to about 600 microns.

In another non-limiting embodiment, the biomass is contacted, in the first step, with oxygen and steam for a period of time that does not exceed 10 seconds. In a further non-limiting embodiment, the biomass is contacted, in the first step, with oxygen and steam for a period of time that does not exceed 3 seconds. In yet another non-limiting embodiment, the biomass is contacted, in the first step, with oxygen and steam for a period of time that does not exceed one second.

As the biomass is contacted with oxygen and steam in the first step, the biomass is oxidized partially, and is decomposed thermally, thereby producing a solid carbonaceous residue, gases such as $CO_2$, steam, and some carbon monoxide (CO) and hydrogen ($H_2$), and vapors of intermediate species such as low molecular weight alkyl and aromatic hydrocarbons, and phenolics as hereinabove described.

When the biomass is contacted with oxygen and steam, in the first step, in the presence of a fluidized bed, the solid carbonaceous residue produced in the first step remains in the fluidized bed and provides the bulk of the exothermal heat of oxidation, thereby maintaining the fluidized bed at the temperatures hereinabove described. The oxygen used in the first step essentially is consumed in such step, while a portion of the carbonaceous residue formed during the first step is consumed as well, and another portion of the carbonaceous residue is entrained as char. The char particles also may contain inorganic materials initially present in the biomass feedstock.

Some cracking of intermediates, i.e., low molecular weight hydrocarbons, phenolics, and aromatics, may occur during the first step; however, higher temperatures are required to convert the residual carbon in the entrained char particles, and additionally to crack and reform the intermediate vapors containing the low molecular weight alkyl and aromatic hydrocarbons, and phenolics. Thus, in a second step, at least a portion of the partially oxidized biomass produced in the first step is treated in the freeboard section of the gasifier with an oxidizing gas comprising oxygen and steam to heat the biomass to a temperature of at least 800° C. to produce synthesis gas.

In a non-limiting embodiment, the partially oxidized and thermally decomposed biomass, in the second step, is heated to a temperature of from about 800° C. to about 1,200° C. In another non-limiting embodiment, the oxidized biomass in the second step, is heated to a temperature of from about 900° C. to about 1,100° C. In yet another non-limiting embodiment, the oxidized biomass, in the second step, is heated to a temperature of from about 925° C. to about 1,000° C.

In a non-limiting embodiment, the oxidizing gas, in the second step, further comprises nitrogen in an amount which does not exceed 60 vol. % of the oxidizing gas. In one non-limiting embodiment, the oxidizing gas includes oxygen-enriched air and steam, in which oxygen is present in an amount of up to about 40 vol. % of the oxidizing gas, and nitrogen is present in an amount that does not exceed 60 vol. % of the oxidizing gas.

In another non-limiting embodiment, the partially oxidized biomass, in the second step, is contacted with oxygen and steam in the absence of nitrogen. In a non-limiting embodiment, oxygen is present in such nitrogen-free gas in an amount which does not exceed 40 vol. %. In yet another non-limiting embodiment, oxygen is present in such nitrogen-free gas in an amount of from about 30 vol. % to about 40 vol. %.

In another non-limiting embodiment, the oxidizing gas, in the second step, further comprises carbon dioxide. In a further non-limiting embodiment, carbon dioxide is present in the oxidizing gas in an amount that does not exceed 20 vol. %. In yet another non-limiting embodiment, carbon dioxide is present in the oxidizing gas in an amount of from about 10 vol. % to about 20 vol. %.

In a further non-limiting embodiment, oxygen is present in such oxidizing gas, in the second step, in an amount of from about 30 vol. % to about 40 vol. %, carbon dioxide is present in the oxidizing gas in an amount of from about 10 vol. % to about 20 vol. %, and the remainder of the oxidizing gas essentially is steam. Trace amounts of argon may be present.

In a non-limiting embodiment, the oxidized biomass, in the second step, is treated with the oxygen and steam for a period of time of from about 0.5 seconds to about 10 seconds. In another non-limiting embodiment, the oxidized biomass, in the second step, is treated with the oxygen and steam for a period of time of from about 4 seconds to about 8 seconds.

Alternatively, in a further non-limiting embodiment, the oxidized biomass, in the second step, is treated with oxygen and steam in a first stage to a temperature of at least 800° C., followed by further treatment with oxygen and steam in a second stage. The oxidized biomass is heated to a temperature in the second stage which is higher than that of the first stage. In a non-limiting embodiment, the oxidized biomass is heated in the first stage to a temperature of at least 800° C. and does not exceed 850° C.

In another non-limiting embodiment, the oxidized biomass is heated in the second stage to a temperature of at least 900° C. In a further non-limiting embodiment, the oxidized biomass is heated in the second stage to a temperature of from about 900° C. to about 1,000° C. In yet another non-limiting embodiment, the oxidized biomass is heated in the second stage to a temperature of from about 925° C. to about 975° C.

In yet another non-limiting embodiment, the oxidized biomass is heated in the first stage to a temperature of from 800° C. to 850° C., and is heated in the second stage to a temperature of from 925° C. to 975° C.

When the oxidized biomass is contacted with oxygen and steam in the second step, whereby the oxidized biomass is heated to a temperature of at least 800° C., carbon in the char is converted fully by the steam to generate hydrogen and carbon monoxide, and steam reforming of the intermediates yields more hydrogen and carbon monoxide. In general, the inorganic materials which are present in the char in general are exposed to temperatures higher than their melting points. Such inorganic materials will melt and stay melted in the char particles. Deposition of char particles and/or inorganic materials on the walls of the gasification vessel is minimal because the particles are entrained under plug flow conditions.

In general, the gasifier is operated at a pressure that does not exceed 10 atm. The fluidized bed section includes particles of a fluidizable material, such as alumina or olivine, having a particle size of from about 50 microns to about 600 microns. Oxygen and steam are introduced into the fluidized bed section of the gasifier to provide a gas velocity of from about 0.7 m/sec. to about 1.5 m/sec., thereby providing a bubbling fluidized bed of the particulate material.

The gas and vapors produced in the fluidized bed section pass through the disengaging zone into the freeboard section, in which the gas and vapors are contacted with oxygen and steam to reach a temperature of from about 925° C. to about 1,000° C. The oxygen and steam are introduced into the freeboard section of the gasifier in such an amount that the velocity of the gaseous phase is maintained from about 0.3 m/sec. to about 0.7 m/sec. In general, gas residence times in the freeboard section of the gasifier are from about 4 seconds to about 8 seconds.

In the freeboard section, the phenolics are converted into simple aromatics, and tar cracking and tar reforming are effected. Carbon in the char essentially is converted fully by the steam and $CO_2$ to generate $H_2$ and CO, and steam reforming of the vapors of the intermediate hydrocarbons also generates $H_2$ and CO. Inorganic materials present in the char will melt. Deposition of inorganic materials on the walls of the gasifier, however, is minimal due to particle entrainment in the existing plug flow regime.

As noted hereinabove, in one alternative non-limiting embodiment, the heating of the partially oxidized biomass to produce synthesis gas may be effected in a combination of a first stage, and a second stage, wherein the partially oxidized biomass is heated to a temperature in the second stage which is greater than that of the first stage.

In one non-limiting embodiment, the first stage is conducted in the freeboard section of the gasifier, and the second stage is conducted in one or more tubular flow reactors. In a non-limiting embodiment, the one or more tubular flow reactor(s) is (are) in the form of refractorized and insulated carbon steel pipes. In another non-limiting embodiment, the heating in the second stage is conducted in two tubular flow reactors which are connected to each other so as to form a U-shaped configuration.

In a non-limiting embodiment, the oxidized biomass is contacted with oxygen and steam in the freeboard section of the gasifier at a temperature of from about 800° C. to about 850° C. The oxygen and steam are introduced into the freeboard section of the gasifier in such amounts that maintain a gaseous velocity of from about 0.3 m/sec. to about 07 m/sec., and the reaction time is from about 4 seconds to about 8 seconds, as hereinabove described, to begin the conversion of the oxidized biomass to a crude synthesis gas. The gas produced in the freeboard section also has char particles entrained therein.

The gas and entrained particles then are passed from the freeboard section of the gasifier to one or more tubular flow reactors. In a non-limiting embodiment, additional oxygen and steam are added to the tubular flow reactor(s). In the tubular flow reactor(s), the gas is heated to a temperature of from about 925° C. to about 975° C., and in general, the reaction time in the tubular flow reactor(s) is from about 1 second to about 2 seconds, which is sufficient to complete the conversion of the oxidized biomass to a crude synthesis gas.

A crude synthesis gas product thus is produced by gasifying biomass in the fluidized bed and freeboard sections of the gasifier, and optionally in one or more tubular flow reactors, under the conditions hereinabove described. Such crude synthesis gas then is conditioned to provide a clean synthesis gas.

In a non-limiting embodiment, crude synthesis gas is cooled, and then passed through one or more cyclones to remove larger particles, such as char particles. In a non-limiting embodiment, the particles removed by the one or more cyclones have a size over 10 microns.

After the particles have been removed from the crude synthesis gas, the crude synthesis gas may be scrubbed in a scrubbing system to remove fines and impurities such as HCl, $H_2S$, and ammonia, as well as sodium salts and tar, to provide a purified synthesis gas. Examples of the preparation of a crude synthesis gas, and of the purification of a crude synthesis gas are described in published PCT Application Nos. WO2010/069068 and WO2009/132449, the contents of which are incorporated by reference.

Once a purified synthesis gas is produced, a portion of the hydrogen and a portion of the carbon monoxide in the synthesis gas are reacted to produce methanol. In a non-limiting embodiment, a portion of the hydrogen and a portion of the carbon monoxide in the synthesis gas are reacted in the presence of a suitable methanol synthesis catalyst, such as a copper oxide based catalyst such as, for example, a $Cu/ZnO/Al_2O_3$ catalyst, to produce methanol.

In one non-limiting embodiment, the hydrogen and carbon monoxide are reacted in the gas phase. In another non-limiting embodiment, the reaction of the hydrogen with carbon monoxide is effected in the gas phase in the presence of a fixed bed of catalyst.

In another non-limiting embodiment, the hydrogen and carbon monoxide are reacted in the liquid phase.

In a non-limiting embodiment, the catalyst may be on stream for at least 5,000 hours before regeneration. In another non-limiting embodiment, the hydrogen and carbon monoxide are reacted to produce methanol at a ratio of hydrogen to carbon monoxide of from about 1:1 to about 3:1.

In a non-limiting embodiment, the hydrogen and carbon monoxide are reacted at a temperature of from about 200° C. to about 260° C. In another non-limiting embodiment, the hydrogen and carbon monoxide are reacted at a pressure of from about 50 atm to about 100 atm.

In another non-limiting embodiment, the hydrogen and carbon monoxide are reacted in the liquid phase in a "three-phrase" reactor. In such an embodiment, the catalyst, which may be a copper oxide based catalyst, such as $Cu/ZnO/Al_2O_3$, is in the form of a fine powder which is suspended in an inert high boiling oil, such as a white mineral oil such as Witco-70 or Drakeol. The hydrogen gas and carbon monoxide gas are dissolved in the oil, and the dissolved molecular species are reacted on the catalytic surfaces of the slurried catalyst. The reactor may be operated under the temperature and pressure conditions hereinabove described.

The methanol then is purified to remove residual hydrogen and carbon monoxide. The purified methanol then is passed to an etherification reactor to produce a product that comprises dimethyl ether.

In a non-limiting embodiment, the etherification of the methanol to produce dimethyl ether is effected in a fixed bed reactor in the presence of a suitable catalyst. In a non-limiting embodiment, the catalyst is an acid catalyst. Suitable catalysts which may be employed include zeolite catalysts, such as, for example, mordenite zeotlites and ZSM-5, gamma alumina, and other acidic catalysts.

In another non-limiting embodiment, the etherification reactor may include, in addition to methanol, inert materials such as nitrogen, methane, synthesis gas, or carbon monoxide. In a non-limiting embodiment, the molar ratio of inert materials to methanol is from about 1:10 to about 1:1.

In another non-limiting embodiment, the etherification of the methanol to dimethyl ether is effected at a temperature of from about 200° C. to about 350° C. In another non-limiting embodiment, the etherification of methanol to dimethyl ether is effected at a pressure of from about 1 atm to about 30 atm.

The dimethyl ether then is purified, whereby water and off-gases, such as methane and ethane, for example, are removed. The purified dimethyl ether then is reacted in a catalytic olefin reactor to produce olefins including ethylene, propylene, and butylene, as well as carbon monoxide, water, and aromatics.

In a non-limiting embodiment, the dimethyl ether is reacted in a fixed bed reactor in the presence of a suitable catalyst to produce olefins, as well as carbon monoxide, water, and aromatics. In a non-limiting embodiment, the catalyst is an acid catalyst. Suitable catalysts which may be employed include zeolite catalysts, gamma alumina, and other acidic catalysts.

In another embodiment, the feed to the olefin reactor may include, in addition to the dimethyl ether, inert materials such as nitrogen or methane. In a non-limiting embodiment, the molar ratio of inert materials to dimethyl ether is from about 1:10 to about 1:1.

In a non-limiting embodiment, the conversion of dimethyl ether to olefins is effected at a temperature of from about 200° C. to about 550° C. In another non-limiting embodiment, the conversion of dimethyl ether to olefins is effected at a pressure of from about 1 atm to about 30 atm.

After the dimethyl ether has been reacted to produce olefins, gases such as carbon monoxide and methane, water, and aromatics are separated from the olefins.

Ethylene then is reacted with a portion of the synthesis gas in a hydroformylation reactor to produce n-propanol, isopropanol, and propionaldehyde. In a non-limiting embodiment, the hydroformylation reactor includes an appropriate catalyst, which in a non-limiting embodiment, is a transition metal-based catalyst. In one non-limiting embodiment, the hydroformylation reactor is a heterogeneous reactor which includes a fixed bed of catalyst. In another non-limiting embodiment, the hydroformylation reactor is a homogeneous reactor, such as a batch reactor or liquid phase reactor.

In a non-limiting embodiment, the ethylene is reacted with a portion of the synthesis gas to produce n-propanol, isopropanol, and propionaldehyde at a temperature of from about 130° C. to about 300° C. In another non-limiting embodiment, the ethylene is reacted with a portion of the synthesis gas to produce n-propanol, isopropanol, and propionaldehyde at a pressure of from about 10 psi to about 400 psi.

After production of the n-propanol, isopropanol, and propionaldehyde from ethylene and synthesis gas, the n-propanol and isopropanol are separated as separate streams from the propionaldehyde. The propionaldehyde then is hydrogenated in a hydrogenation reactor to produce n-propanol. In a non-limiting embodiment, the hydrogenation of propionaldehyde to produce n-propanol is carried out in a fixed bed reactor that contains an appropriate catalyst. Suitable catalysts include, but are not limited to, transition metal catalysts, such as, for example, Pd, Pt, and Rh.

In another non-limiting embodiment, the hydrogenation reaction is effected at a hydrogen to propionaldehyde molar ratio of from about 1:25 to about 1:5. In yet another non-limiting embodiment, the hydrogenation reaction is effected at a hydrogen to propionaldehyde molar ratio of about 1:10. In another non-limiting embodiment, the hydrogenation reaction is effected at a temperature of from about 150° C. to about 250° C. In yet another non-limiting embodiment, the hydrogenation reaction is effected at a pressure of from about 1 atm to about 50 atm. n-propanol then is recovered, and unreacted propionaldehyde is recycled to the hydrogenation reactor.

The invention now will be described with respect to the drawing, wherein:

FIG. 1 is a schematic of a process for producing n-propanol in accordance with an embodiment of the present invention.

Referring now to the drawings, a biomass feed in line 11 is fed to a gasification unit 12 to provide a crude synthesis gas. The crude synthesis gas is withdrawn from gasification unit 12 through line 13, and is subjected to thermal reforming in reformer 14 to provide additional synthesis gas. The resulting crude synthesis gas is withdrawn from reformer 14 through line 15, and is subjected to a series of purification steps, indicated schematically as 16. The purified synthesis gas then is passed to line 17 and into three phase methanol reactor 18. Prior to being passed into methanol reactor 18, a portion of the purified synthesis gas is withdrawn from line 17 through line 22.

In the methanol reactor 18, the carbon monoxide and hydrogen of the purified synthesis gas is reacted to produce methanol. The methanol-containing product is withdrawn from reactor 18 through line 19, and is subjected to a purification process, indicated schematically as 20. Carbon monoxide and hydrogen are separated from the methanol, and recycled through line 21 to line 17. A purified methanol product is passed through line 23 to etherification reactor 24, wherein the methanol is reacted to form an etherification product including dimethyl ether, or DME. The etherification product is withdrawn from etherification reactor 24 through line 25 and is subjected to a series of separation steps, indicated schematically as 26. Off-gases are withdrawn through line 27, water is withdrawn through line 28, and dimethyl ether is withdrawn through line 29 and passed to catalytic olefin reactor 30, wherein the dimethyl ether is reacted to produce a plurality of olefins as well as carbon monoxide, methane, water, and aromatics. The olefin-containing product is withdrawn from olefin reactor 30 through line 31 and then subjected to a series of separation steps, indicated schematically at 32. Gases such as carbon monoxide and methane are withdrawn through line 33, water is withdrawn through line 34, aromatics are withdrawn through line 35, and butylene is withdrawn through line 36. Propylene is withdrawn through line 37. Ethylene is withdrawn from line 38 and the ethylene is passed to hydroformylation reactor 39. In hydroformylation reactor 39, ethylene is reacted with a portion of the purified synthesis gas in line 22 to produce a product including propionaldehyde, n-propanol, and isopropanol. The product including propionaldehyde, n-propanol, and isopropanol is withdrawn from hydroformylation reactor 39 through line 40, and subjected to separation steps, indicated schematically as 41. Isopropanol is recovered from line 42. n-propanol is recovered from line 43. Propionaldehyde in line 44 is passed to hydrogenation reactor 46, wherein the propionaldehyde is reacted with hydrogen from line 45 to produce a product including n-propanol. The product including n-propanol is withdrawn from hydrogenation reactor 46 through line 47, and is subjected to a separation process, indicated schematically at 48. Propionaldehyde in line 49 is recycled to line 44. n-propanol is recovered in line 50, and mixed with the n-propanol in line 43.

The disclosures of all patents and publications, including published patent applications, are incorporated herein by reference as if each patent and publication were incorporated individually by reference.

It is to be understood, however, that the scope of the present invention is not to be limited to the specific embodiments described above. The invention may be practiced other than as particularly described and still be within the scope of the accompanying claims

What is claimed is:

1. A process for producing at least one alcohol having three carbon atoms, from a carbonaceous material, comprising:
    (a) gasifying said carbonaceous material to provide a crude synthesis gas;
    (b) purifying said crude synthesis gas to provide a purified synthesis gas;
    (c) reacting at least a portion of the carbon monoxide with a portion of the hydrogen from said purified synthesis gas to provide methanol and wherein said carbon monoxide and said hydrogen are reacted in a reactor in the presence of a catalyst suspended in an inert oil having a boiling point;
    (d) reacting said methanol to produce a product comprising dimethyl ether;
    (e) purifying the product of step (d) to provide purified dimethyl ether;
    (f) reacting said dimethyl ether in the presence of a catalyst in a fixed bed catalytic reactor to provide at least one olefin comprising ethylene;
    (g) reacting said ethylene with synthesis gas in a hydroformylation reactor containing a fixed bed of catalyst to provide a product comprising n-propanol, isopropanol, and propionaldehyde;
    (h) separating said n-propanol and said isopropanol as separate streams from said propionaldehyde;
    (i) hydrogenating said propionaldehyde in a hydrogenation reactor to provide a product comprising n-propanol and unreacted propionaldehyde;
    (j) separating said unreacted propionaldehyde from said n-propanol produced in step (i) to provide a product comprising n-propanol; and
    (k) recycling said unreacted propionaldehyde to step (i).

2. The process of claim 1 wherein said carbonaceous material is biomass.

3. The process of claim 2 wherein, in step (a), said biomass is heated in a first step to a temperature of at least 500° C. and no greater than 1,000° C. to produce a partially oxidized biomass, and said partially oxidized biomass is heated in a second step to a temperature of from about 800° C. to about 1,200° C. to provide a crude synthesis gas.

4. The process of claim 3 wherein said biomass is heated in said first step to a temperature of at least 550° C. and no greater than 900° C.

5. The process of claim 4 wherein said biomass is heated in said first step to a temperature of at least 600° C. and no greater than 800° C.

6. The process of claim 5 wherein said biomass is heated in said first step to a temperature of at least 600° C. and no greater than 700° C.

7. The process of claim 6 wherein said biomass is heated in said first step to a temperature of about 690° C.

8. The process of claim 7 wherein said partially oxidized biomass is heated in said second step to a temperature of from about 900° C. to about 1,100° C.

9. The process of claim 8 wherein said partially oxidized biomass is heated in said second step to a temperature of from about 925° C. to about 1,000° C.

10. The process of claim 1 wherein, in step (c), carbon monoxide and hydrogen from a first portion of said purified synthesis gas are reacted to provide methanol, and in step g, said ethylene is reacted with a second portion of said purified synthesis gas in a hydroformylation reactor to provide a product comprising at least one alcohol having three carbon atoms.

11. The process of claim 1 wherein, in step (c), essentially all of the carbon monoxide and essentially all of the hydrogen of said purified synthesis gas from step (b) are reacted to provide methanol, and in step g, said ethylene is reacted with a synthesis gas, other than said purified synthesis gas of step (b), in a hydroformylation reactor to provide a product comprising at least one alcohol having three carbon atoms.

12. The process of claim 11 wherein said synthesis gas of step (g) is produced by (i) subjecting natural gas to steam reforming to provide a crude synthesis gas, and (ii) purifying the crude synthesis gas of step (i) to provide a purified synthesis gas.

13. The process of claim 1 wherein said catalyst is a $Cu/ZnO/Al_2O_3$ catalyst.

14. The process of claim 1 wherein, in step (c), said carbon monoxide and said hydrogen are reacted at a temperature of from about 200° C. to about 260° C.

15. The process of claim 1 wherein, in step (c), said carbon monoxide and said hydrogen are reacted at a pressure of from about 50 atm to about 100 atm.

16. The process of claim 1 wherein, in step (d), said methanol is reacted in the presence of a catalyst in a fixed bed reactor.

17. The process of claim 16 wherein said catalyst is selected from the group consisting of mordenite zeolites, ZSM-5, and gamma alumina.

18. The process of claim 1 wherein, in step (d), said methanol is reacted at a temperature of from about 200° C. to about 350° C.

19. The process of claim 1 wherein, in step (d), said methanol is reacted at a pressure of from about 1 atm to about 30 atm.

20. The process of claim 1 wherein, in step (f), said catalyst is selected from the group consisting of zeolite catalysts and gamma alumina.

21. The process of claim 1 wherein, in step (f), said dimethyl ether is reacted in the presence of inert materials.

22. The process of claim 21 wherein said inert materials include nitrogen and methane.

23. The process of claim 22 wherein, in step (f), the molar ratio of said inert materials to said dimethyl ether is from about 1:10 to about 1:1.

24. The process of claim 1 wherein, in step (f), said at least one olefin further comprises propylene and butylene.

25. The process of claim 1 wherein, in step (f), said dimethyl ether is reacted at a temperature of from about 200° C. to about 550° C.

26. The process of claim 1 wherein, in step (f), said dimethyl ether is reacted at a pressure of from about 1 atm to about 30 atm.

27. The process of claim 1 wherein, in step (g), said ethylene is reacted at a temperature of from about 130° C. to about 300° C.

28. The process of claim 1 wherein, in step (g), said ethylene is reacted at a pressure of from about 10 psi to about 400 psi.

29. The process of claim 1 wherein, in step (g), said ethylene is reacted in the presence of a transition metal catalyst.

30. The process of claim 1 wherein, in step (i), said propionaldehyde is hydrogenated in the presence of a catalyst.

31. The process of claim 30 wherein said catalyst is a transition metal catalyst.

32. The process of claim 31 wherein said transition metal catalyst is selected from the group consisting of palladium, platinum, and rhodium.

33. The process of claim 1 wherein, in step (i), said propionaldehyde is hydrogenated at a hydrogen to propionaldehyde molar ratio of from about 1:25 to about 1:5.

34. The process of ,claim 1 wherein said propionaldehyde is hydrogenated at a hydrogen to propionaldehyde molar ratio of about 1:10.

35. The process of claim 1 wherein, in step (i), said propionaldehyde is hydrogenated at a temperature of from about 150° C. to about 250° C.

36. The process of claim 1 wherein, in step (i), said propionaldehyde is hydrogenated at a pressure of from about 1 atm to about 50 atm.

\* \* \* \* \*